(12) United States Patent
St. George et al.

(10) Patent No.: US 9,918,728 B2
(45) Date of Patent: Mar. 20, 2018

(54) STONE FRAGMENT SUCTION DEVICE

(71) Applicant: Gyrus Acmi, Inc., Southborough, MA (US)

(72) Inventors: Lawrence J. St. George, Sudbury, MA (US); Kurt G. Shelton, Woburn, MA (US); Kester J. Batchelor, Mound, MN (US)

(73) Assignee: Gyrus ACMI, Inc., Southborough, MA (US)

( * ) Notice: Subject to any disclaimer, the term of this patent is extended or adjusted under 35 U.S.C. 154(b) by 202 days.

(21) Appl. No.: 14/693,037

(22) Filed: Apr. 22, 2015

(65) Prior Publication Data

US 2015/0305759 A1 Oct. 29, 2015

Related U.S. Application Data

(60) Provisional application No. 61/983,164, filed on Apr. 23, 2014.

(51) Int. Cl.
*A61M 25/01* (2006.01)
*A61M 25/08* (2006.01)
(Continued)

(52) U.S. Cl.
CPC .......... *A61B 17/22012* (2013.01); *A61B 1/07* (2013.01); *A61B 17/22* (2013.01);
(Continued)

(58) Field of Classification Search
CPC ..... A61B 1/07; A61B 17/22; A61B 17/22012; A61B 2017/22051; A61B 2017/22069;
(Continued)

(56) References Cited

U.S. PATENT DOCUMENTS 5,078,681 A * 1/1992 Kawashima ....... A61B 1/00082
604/103.11
5,273,526 A 12/1993 Dance et al.
(Continued)

FOREIGN PATENT DOCUMENTS

WO WO 93/00119 A1 1/1993
WO WO 2009/117663 A2 9/2009
(Continued)

OTHER PUBLICATIONS

International Search Report, PCT/US2015/027006, Jun. 19, 2015, p. 5.
(Continued)

*Primary Examiner* — Adam Marcetich
(74) *Attorney, Agent, or Firm* — Chapin IP Law, LLC

(57) ABSTRACT

Apparatus and methods for a stone fragment suction device are provided with fluid flow paths at a distal tip to encourage creation of turbulence or a vortex to enhance stone dust or debris removal via directed flow using targeted fluid exit conduits. An apparatus includes a steerable access sheath having a proximal end and a distal end, a tip at the distal end, directed flow channels at the distal tip, and a suction conduit positioned within a central lumen of the steerable access sheath from the distal end to the proximal end, the steerable access sheath containing an outer lumen surrounding the central lumen with one or more channels therethrough, the steerable access sheath may further include a radiopaque material at the distal end or along a length of the steerable access sheath to enable tracking with a remote fluoroscopic device.

19 Claims, 11 Drawing Sheets

(51) Int. Cl.
*A61B 17/22* (2006.01)
*A61B 1/07* (2006.01)

(52) U.S. Cl.
CPC .... *A61M 25/0108* (2013.01); *A61M 25/0147* (2013.01); *A61B 2017/22051* (2013.01); *A61B 2017/22069* (2013.01); *A61B 2017/22079* (2013.01); *A61B 2017/22084* (2013.01)

(58) Field of Classification Search
CPC .......... A61B 2017/22079; A61B 2017/22084; A61M 25/0108; A61M 25/0147; A61M 25/0074; A61M 25/0075; A61M 2025/105; A61M 25/0015; A61M 25/007; A61M 2210/1078; A61M 25/0136
See application file for complete search history.

(56) References Cited

U.S. PATENT DOCUMENTS

| | | | | |
|---|---|---|---|---|
| 5,415,636 | A * | 5/1995 | Forman | A61M 25/104 604/101.03 |
| 6,280,413 | B1 * | 8/2001 | Clark | A61F 2/013 604/102.01 |
| 6,533,763 | B1 * | 3/2003 | Schneiter | A61M 25/007 604/264 |
| 6,669,679 | B1 * | 12/2003 | Savage | A61M 25/007 604/131 |
| 2002/0077594 | A1 * | 6/2002 | Chien | A61M 25/10 604/103.02 |
| 2003/0032937 | A1 * | 2/2003 | Griego | A61M 25/0026 604/508 |
| 2003/0171765 | A1 * | 9/2003 | Kokate | A61B 17/22 606/159 |
| 2004/0204629 | A1 | 10/2004 | Knapp | |
| 2005/0085769 | A1 | 4/2005 | MacMahon et al. | |
| 2007/0060879 | A1 * | 3/2007 | Weitzner | A61B 17/12045 604/95.04 |
| 2007/0073271 | A1 * | 3/2007 | Brucker | A61M 25/0041 604/537 |
| 2008/0139897 | A1 * | 6/2008 | Ainsworth | A61B 5/0084 600/300 |
| 2008/0249522 | A1 * | 10/2008 | Pappone | A61B 18/18 606/41 |
| 2012/0004596 | A1 * | 1/2012 | Thomas | A61B 17/32075 604/22 |
| 2013/0018314 | A1 * | 1/2013 | Teague | A61M 25/007 604/151 |
| 2013/0023802 | A1 * | 1/2013 | McIntosh | A61M 25/10 601/2 |
| 2013/0046282 | A1 * | 2/2013 | O'Day | A61M 25/007 604/508 |
| 2013/0131445 | A1 * | 5/2013 | Zerfas | A61B 17/22 600/104 |
| 2014/0018691 | A1 * | 1/2014 | McNeill | A61M 16/04 600/532 |
| 2015/0018937 | A1 * | 1/2015 | Lagodzki | A61M 25/0021 623/1.24 |

FOREIGN PATENT DOCUMENTS

WO    WO 2011/158232    12/2011
WO    WO 2012/009187 A1    1/2012

OTHER PUBLICATIONS

The State Intellectual Property Office of China, Office Action for Application No. 201580000812.9, dated May 27, 2017, p. 8.

* cited by examiner

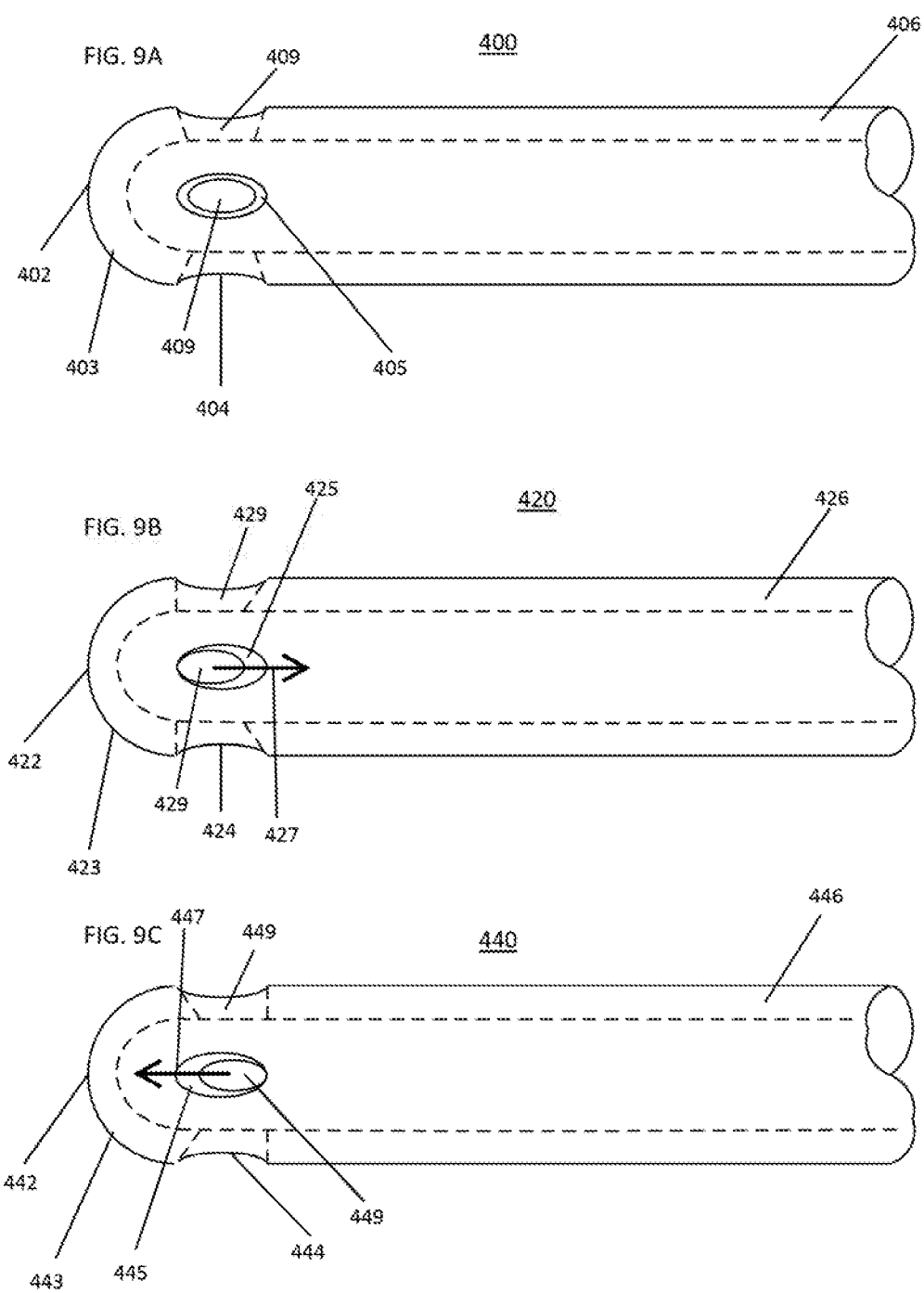

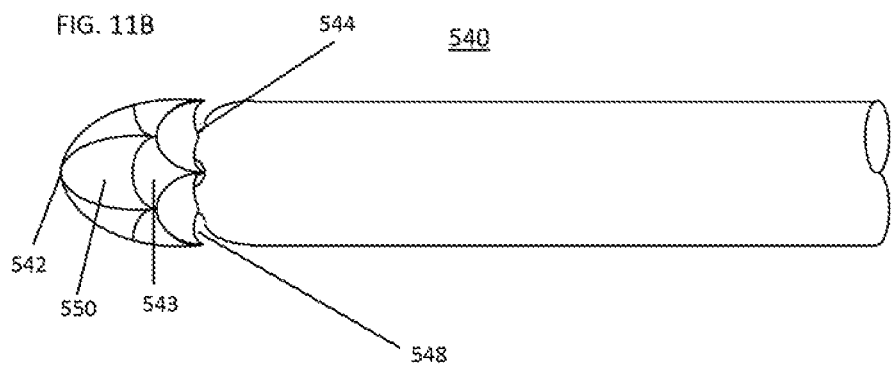
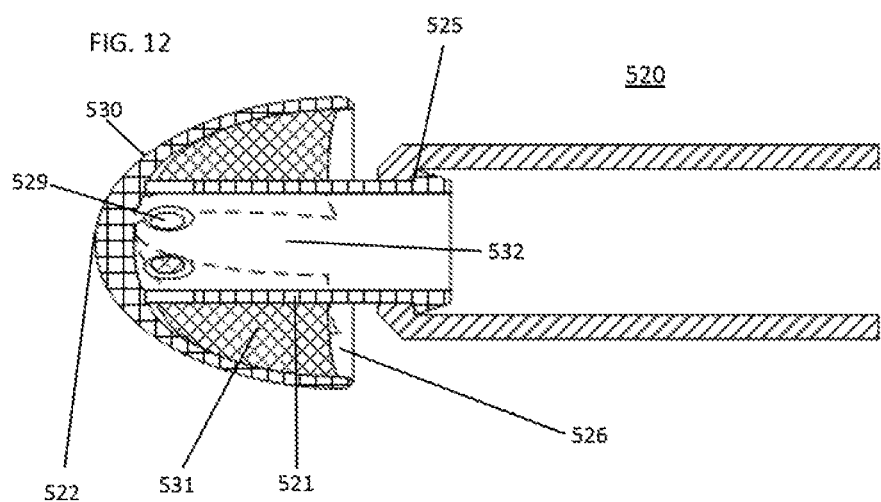
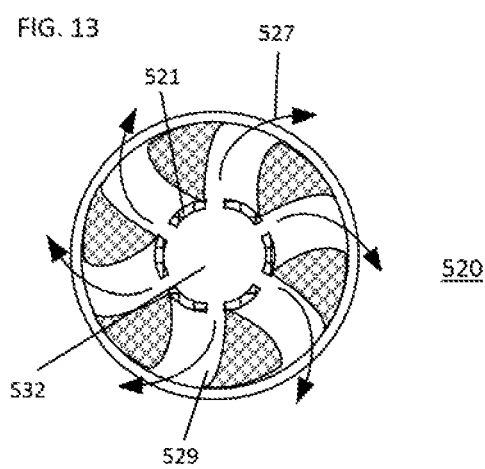

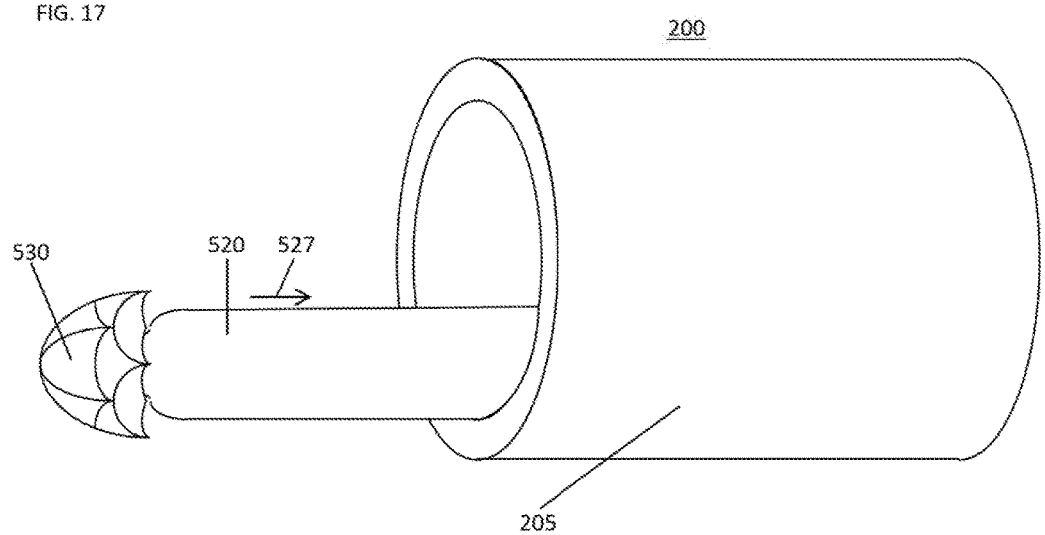

_(10)_ STONE FRAGMENT SUCTION DEVICE

BACKGROUND OF THE INVENTION

The present invention generally relates to a kidney device, and more specifically to a stone fragment suction device.

In general, one purpose of a human kidney is to filter waste products from the blood and excrete these substances and excess water in the form of urine. A calyx section of the kidney generally refers to a beginning of the urine collecting system. A kidney typically has 6-10 calyces. Stones in the kidney are typically found within the calyx. In general, a stone is a microscopic organized aggregation of salts. Procedures to treat the presence of kidney stones may include, for example, lithotripsy and ureteroscopy.

Ureteroscopy is a practice used to diagnose the presence of kidney stones or to provide access for other devices such as lithotripters, graspers, or stone baskets. Small stones may be treated with only a stent (no lithotripsy) (e.g. 3 mm or smaller), by dilating the ureter. However, if the stone is large (e.g. 5 mm or larger), continues to cause problems, or the urinary system appears infected, a urologist may elect to perform a stone lithotripsy procedure after which an endoscope is used to place a small stent in the ureter. This stent allows urine to pass, which can alleviate pain, and dilates the ureter, thus potentially allowing small stones to pass as mentioned above.

Treatment of kidney stones with ureteroscopic lithotripsy or laser fibers creates stone fragments and stone dust or "sand." Stone baskets or graspers may have problems removing stone fragments that are below 2 mm in size. When small stones and stone dust are present in the more difficult to access calyces of the kidney, it would be desirable to have a more robust removal mechanism. In these cases, unless the small stones and stone dust are removed, they can continue to grow and aggregate until they become symptomatic and require more invasive treatment.

Therefore, what is needed is a device and method of mechanically removing kidney stone fragments and stone dust or "sand" in order to reliably reduce the amount of fragmented kidney stones left in a patient, particularly following treatment with ureteroscopic lithotripsy or laser fibers.

SUMMARY OF THE INVENTION

The following presents a summary of the innovation in order to provide a basic understanding of some aspects of the invention.

The present invention provides methods and apparatus for a stone fragment suction device.

In general, in one aspect, the invention features an apparatus including a steerable access sheath having a proximal end and a distal end, a tip at the distal end, and a suction conduit positioned within a central lumen of the steerable access sheath from the distal end to the proximal end, the steerable access sheath containing an outer lumen surrounding the central lumen with one or more channels therethrough, an outer circumference of the outer lumen and an outer circumference of the central lumen forming concentric circles, and the steerable access sheath further including a radiopaque material at the distal end or along a length of the steerable access sheath to enable tracking with a remote fluoroscopic device. In other embodiments, the central lumen is provided offset from a central longitudinal axis of the outer lumen or as a noncircular shaped channel, for example with an ovular cross section. An ovular cross section may be desirable to provide more surface area while staying within certain guidelines for Fr (French) size in order to fit within an endoscope. It is further contemplated that the device may be used independent of an endoscope and may have a larger diameter as a result.

Embodiments of the invention may have one or more of the following advantages.

The apparatus of the present invention provides a mechanical means of removing sand and small fragments of kidney stones without the need of baskets.

The apparatus of the present invention reduces the amount of fragmented kidney stones left in a patient.

The apparatus of the present invention may eliminate the need for direct visualization of a suction device and the materials it is removing and accommodates fluoroscopic evaluation by employing a radiopaque material in a tip or through a body of the apparatus. By incorporating the radiopaque material in the tip or through the body of the apparatus, a user can locate a suction device within a patient without direct visualization.

The apparatus of the present invention may include a suction conduit configured in different diameters along its length to minimize the incidence or frequency of fragments from becoming lodged within the suction conduit. For example, the suction conduit may be narrower at a distal end and widen toward a proximal end.

The apparatus of the present invention may include a fluid outflow line which may be designed to target equal fluid outflow and suction inflow to prevent or limit the potential for pressure drops or collapses in a kidney during use.

The apparatus of the present invention may include a clear section on the suction conduit to enable visual confirmation of sand and fragment removal. This clear section can be configured as a chamber and include one or more particle filters to enable sand and fragment quantification and collection. The clear section may help indicate to a user if the suction conduit is clogged.

Accordingly, pursuant to one aspect of the present invention, there is contemplated an apparatus comprising a steerable access sheath, the steerable access sheath comprising a proximal end, a distal end, a tip at the distal end, a central lumen, and an outer lumen surrounding the central lumen; a suction conduit positioned within the central lumen disposed from the distal end to the proximal end; the outer lumen having one or more channels therethrough; at least a portion of the one or more channels being fluid flow channels; the one or more fluid flow channels extending from the proximal end to the distal end, the one or more fluid flow channels including one or more targeted exit conduits and in fluid communication with the one or more fluid flow channels proximal to the tip, and the one or more targeted exit conduits having exit pathways oriented to create a directed flow at the distal tip.

The invention may be further characterized by one or any combination of the features described herein, such as the one or more targeted exit conduits are configured to generate turbulence at least one of the one or more targeted exit conduits are angled toward the distal end of the steerable access sheath, at least one of the one or more targeted exit conduits are angled toward the proximal end of the steerable access sheath, at least one of the one or more targeted exit conduits are angled exactly orthogonal to the longitudinal axis of the steerable access sheath, the one or more targeted exit conduits are arranged in a single plane parallel to a cross section of the steerable access sheath, the one or more targeted exit conduits are arranged in multiple planes parallel to the cross section of the steerable access sheath, the angle of the targeted exit conduits with respect to the longitudinal axis of the steerable access sheath varies across each of the one or more targeted exit conduits, the tip further comprises a soft edge for ease of insertion, the tip further comprises a mushroom shaped flap, the mushroom shaped flap collapses to a collapsed state during insertion and expands to expanded state during active fluid flow, the mushroom shaped flap further comprises an exit port for fluid flow at a distal most end of the steerable access sheath, the suction conduit is tapered with decreasing diameters from the proximal end to the distal end of the steerable access sheath, the tip is selectively deflectable to enable specific placement of the suction conduit, the suction conduit comprises a steering mechanism selected from the group consisting of one or more cables and a lockable control actuator, the steerable access sheath further comprises an anchoring mechanism to prevent a migration of the steerable access sheath during active suction, a channel positioned within the outer lumen of the steerable access sheath from the distal end to the proximal end, and one or more fiberoptic imaging fibers positioned within a length of the lumen.

Accordingly, pursuant to another aspect of the present invention, there is contemplated an apparatus comprising an access sheath, the access sheath comprising: a proximal end, a distal end, a tip at the distal end, a central lumen, and an outer lumen; a suction conduit positioned within the central lumen from the distal end to the proximal end; a radiopaque material at the distal end to enable tracking with a remote fluoroscopic device; the outer lumen having one or more channels therethrough; at least a portion of the one or more channels being fluid flow channels, the one or more fluid flow channels extending from the proximal end to the distal end, the one or more fluid flow channels including a plurality of targeted exit conduits at a distal end.

The invention may be further characterized by one or any combination of the features described herein, such as the central lumen and the outer lumen form concentric circles, the access sheath has a preformed tip angle, the suction conduit comprises at least half the volume of the access sheath.

Accordingly, pursuant to another aspect of the present invention, there is contemplated a method for removing stone dust and stone debris from a patient, comprising inserting the steerable access sheath, as described above, into a patient; steering the removable access sheath to an area of interest; directing fluid through the one or more fluid flow channels and creating turbulence at the tip through the targeted exit conduits; and using active suction to remove the stone dust and stone debris.

These and other features and advantages will be apparent from a reading of the following detailed description and a review of the associated drawings. It is to be understood that both the foregoing general description and the following detailed description are explanatory only and are not restrictive of aspects as claimed.

BRIEF DESCRIPTION OF THE DRAWINGS

The invention will be more fully understood by reference to the detailed description, in conjunction with the following figures, wherein:

FIGS. 9A-9C are cross-sectional views of embodiments of the present invention that target different exit angles for directed fluid flow.

FIG. 11b is a side view of an embodiment of the present invention.

FIG. 12 is a cross sectional view of an embodiment of the present invention.

FIG. 13 is a cross sectional view of an embodiment of the present invention.

FIG. 17 is a perspective view of an embodiment of the present invention.

DETAILED DESCRIPTION

Figure 1:
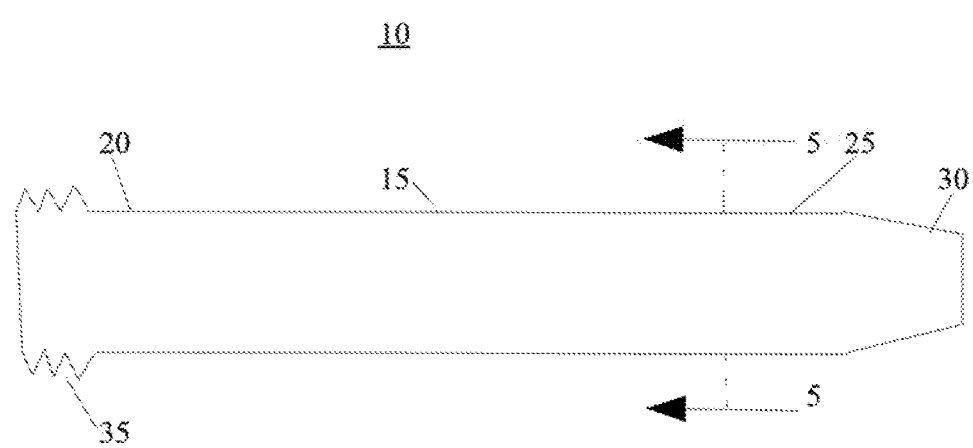
FIG. 1 is a side elevation view of a first exemplary stone fragment suction device of the present invention.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without some of these specific details. In other instances, well-known structures and devices are shown in block diagram form in order to facilitate describing the present invention.

As shown in FIG. 1, a first exemplary stone fragment suction device 10 includes a steerable access sheath 15 having a proximal end 20 and a distal end 25. The distal end 25 includes a tip section 30.

The tip section 30 may be configured with a chamfered and soft edge for ease of insertion into the ureteral orifice of a human kidney. In one specific embodiment, the chamfered edge and soft edge of the tip section 30 includes a restricted opening. It is contemplated that the tip of the stone fragment suction device 10 may further comprise a preformed tip angle. Such a preformed tip angle would allow passive steering through rotation of the stone fragment suction device 10. Rotating the stone fragment suction device about the longitudinal axis would allow the preformed angle at the tip to rotate to different positions about the longitudinal axis and this may help to navigate through and into difficult to reach locations. The combination of rotation of the preformed tip angle and use of active deflection may facilitate easier navigation through tortuous pathways.

The stone fragment suction device 10 may include a radiopaque material at a tip section 30 or along its length that enables a user to identify a location of the stone fragment suction device 10 relative to a patient's body using fluoroscopic techniques.

The proximal end 20 may include a suction connection 35. The suction connection 35 is configured to provide a connection of the proximal end 20 of the steerable access sheath 15 to a suction plug (not shown) or a removable suction receptacle (not shown). The removable suction receptacle enables a collection of materials suctioned through a suction conduit, fully described below. The removable suction receptacle may be equipped with a disconnectable filter used to separate particles of different sizes within the removable suction receptacle to more easily facilitate stone pathology analysis. It is contemplated that the suction conduit may also function as an irrigation channel and one channel may be interchangeably used for both purposes. It is contemplated that it may be desirable to monitor the fluid outflow into the patient and the fluid inflow out of the patient to ensure that excess fluid is not left within a patient's kidney or that excess fluid is removed.

Figure 2:
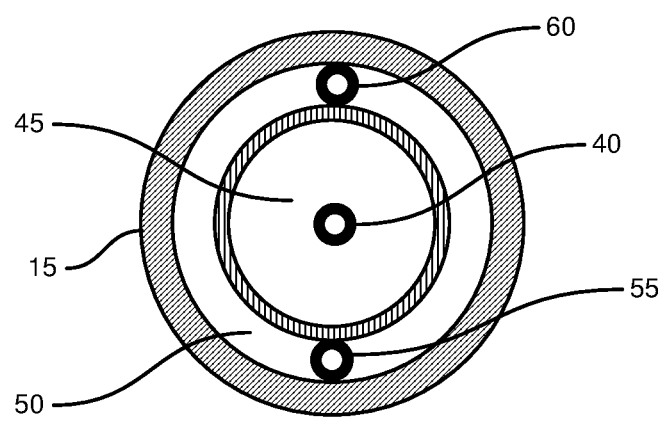
FIG. 2 is a sectional view taken along line 5-5 in FIG. 1.

As shown in FIG. 2, extending longitudinally through the steerable access sheath 15 from the distal end 25 to the proximal end 20 is a suction conduit 40 positioned within a central lumen 45. It is contemplated that the size of the suction conduit may be variable depending on whether or not the internal fluid channel is in an expanded or contracted state. When fluid is actively flowing through the internal fluid channel, which may be positioned within central lumen 45, internal fluid channel may expand to allow fluid to flow along the length. Internal fluid channel may be made of compressible material, material that folds over itself, stretchable material, or the like. When internal fluid channel is not in active use (i.e. no fluid flow), internal fluid channel may enter a contracted state allowing central lumen 45 more surface area for active suction of stone particles and stone debris. It is contemplated that the size of the suction conduit may be variable along the length of the ureteral access sheath. It is contemplated that the suction conduit may comprise greater than 50% of the total volume of the ureteral access sheath or less than 50% of the total volume of the ureteral access sheath, preferably greater than 50% of the total volume of the ureteral access sheath to allow for passage of larger stones. The steerable access sheath 15 also includes an outer lumen 50 surrounding the central lumen 45 and containing one or more channels 55, 60 therethrough. While this embodiment is shown to include two channels 55, 60, other embodiments may include additional channels within the outer lumen 50.

In one embodiment, the suction conduit 40 is tapered with decreasing diameters from the proximal end 20 to the distal end 25 of the steerable access sheath 15. This tapering of the suction conduit 40 minimizes a potential for stone fragments being lodged within the suction conduit 40.

Figure 3:
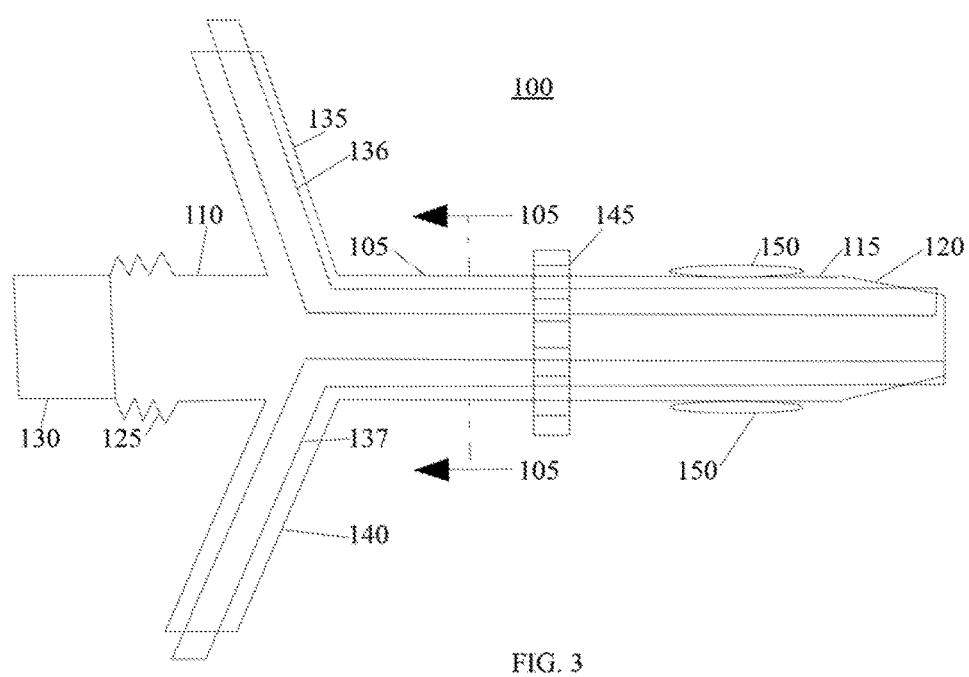
FIG. 3 is a side elevation view of a second exemplary stone fragment suction device of the present invention.

As shown in FIG. 3, a cross section of a second exemplary stone fragment suction device 100 includes a steerable access sheath 105 having a proximal end 110 and a distal end 115. The distal end 115 includes a tip section 120. The tip section 120 includes a radiopaque material that enables a user to identify a suction device as well as the tip section's 120 location relative to a patient's body using fluoroscopic techniques.

The proximal end 110 includes a suction connection 125 adapted to receive a removable suction plug 130 or sample jar (not shown). An optional adapter 135 and an inflow adapter 140 are positioned on approximately opposite sides of the steerable access sheath 105 near the proximal end 110. Both adapters 135, 140 enable an introduction of fluid, steering mechanisms, and other materials, through channels 136, 137, respectively.

Optionally, anterior to the optional adapter 135 and an inflow adapter 140 there is a steering mechanism 145 surrounding the steerable access sheath 105. In some embodiments, also included on the steerable access sheath 105 is an anchoring device 150, such as, for example, an inflation balloon, one or more retractable tines, a fixed spiral, an inflatable spiral, a spiral which may be driven under power, and so forth. Spiral technology used for this purpose is taught in U.S. Pat. No. 5,601,537, the contents of which are incorporated by reference in their entirety. The anchoring device may be located at a distal region of the device, located along the length of the device, or both. The anchoring device 150 may be used to prevent migration of the steerable access sheath 105 during an active suction procedure. In the case where the anchoring mechanism is a power spiral, a fixed spiral, or an inflatable spiral, the spiral may be used to move the access sheath into position through the tortuous pathways within an anatomical region of interest.

Figure 4:
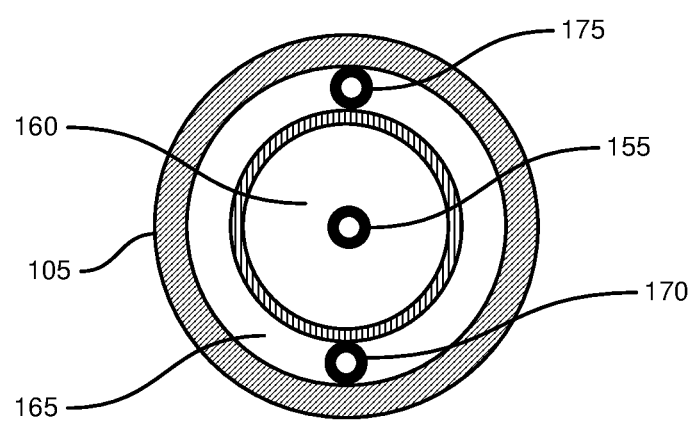
FIG. 4 is a sectional view taken along line 105-105 in FIG. 3.

As shown in FIG. 4, extending longitudinally through the steerable access sheath 100 along line 105-105 from the distal end 115 to the proximal end 110 is a suction conduit 155 positioned within a central lumen 160. In an embodiment, the suction conduit 155 includes a clear section to enable visual confirmation/observation of sand and fragment removal. This clear section may include a chamber housing a particle filter to enable quantification and collection of sand and fragments. The steerable access sheath 105 also includes an outer lumen 165 surrounding the central lumen 160 with one or more channels 170, 175 therethrough. While this embodiment is shown to include two channels 170, 175, other embodiments may include one or more additional channels within the outer lumen 165.

In one example, channel 170 is a fluid inflow channel connected to the inflow adapter 140 that provides a link to an external source of fluid (not shown). In an embodiment, this fluid outflow channel 170 is configured to collapse when there is no fluid flow. In another embodiment, the fluid inflow channel is a flexible tube expandable into the suction conduit 155 during active fluid infusion.

In one embodiment, an internal portion of the fluid inflow channel 170 is rigid. In another embodiment, the internal portion of the fluid inflow channel 170 may expand radially during active fluid flow. In some embodiments, the fluid inflow channel may be in one or multiple lumens and may be within another lumen internal to the suction conduit 155.

In still another embodiment, only a proximal portion of the suction conduit 155 is selectively collapsed, pinched off, or incorporates a mechanism for halting or reducing suction flow such that the fluid inflow channel 170 is used to temporarily increase pressure or distend the distal portion of the suction conduit 155 to free fragments that may become lodged in the suction conduit 155. In one particular embodiment, the suction conduit 155 is designed to permit alternating a direction of fluid flow.

In another embodiment, since a human kidney is susceptible to both higher and lower pressures, the suction conduit 155 includes a closed loop design to keep a pressure ratio between inflow and outflow volume close to one. In some embodiments, this may involve the use of a feedback mechanism and/or a user display indicating volume of fluid in and volume of fluid out. It is contemplated that a pressure sensor may be located in the distal region of the tip of the suction conduit or outer sheath.

Incorporation of another channel in the outer lumen 165 surrounding the central lumen 160 provides an additional port enabling a user to selectively add other liquids to the fluid inflow channel 170, which is linked to the channel 137 of the inflow adapter 140. This may be advantageous for the inclusion of materials such as those used in fluoroscopic contrast. In some applications, as vacuuming progresses, a user may introduce contrast to the inflow to better identify a location of any remaining stones or sand.

In one embodiment, fiberoptic imaging in the form of fiberoptic and illumination bundles are included in channel 175. The fiberoptic and illumination bundles can include, for example, separate fibers or be multiplexed on the same fibers.

Referring again to FIG. 3, in an illustrative embodiment, the tip section 120 has a chamfered and soft edge for ease of insertion. The chamfer may also provide a restricted opening, either by step down in size or some form of grill, to the suction conduit 155. In an alternate embodiment, the chamfered edge of the tip section 120 may have no effect on the suction conduit 155 while another form of suction conduit 155 step down or restriction is included.

The suction conduit 155 may be constructed to have different diameters along its length. For example, the diameters of the suction conduit 155 can decrease from a larger diameter in a ureterovesical junction to a smaller diameter in the distal portion 115 of the suction conduit 155. This configuration minimizes a potential for fragments being jammed as they enter the suction conduit 155 at the tip section 120.

In one embodiment, the fluid inflow channel 170 and suction conduit 155 are configured to create turbulence or a vortex to improve stone removal performance. It is contemplated that the addition of a syringe or alternative device to create force and provide faster fluid outflow speeds may be desirable in the creation of turbulence or a vortex within the kidney. The turbulence or vortex may stir up stone fragments or stone dust which may help in flushing out the kidney. Targeted exit conduits provided in the present invention may be able to better concentrate inflow liquid on the far side of a stone burden from the outflow orifice and thus more easily directly "wash" or "push" the stone burden toward the outflow orifice.

Any removal of fluid from the ureter or calyx can cause a pressure drop and potentially collapse the kidneys, renal pelvis, ureter, calyx, and so forth. To overcome this, the fluid inflow channel 170 can be used to introduce saline or other fluid to prevent such a collapse.

The suction conduit 155 can be used as a ureteral access sheath and have a large enough lumen to accommodate ureteroscopes. Typically, ureteral access sheaths are not advanced in a kidney beyond the ureteral pelvic junction. Embodiments of the suction conduit 155 described herein, particularly those embodiments including a steering mechanism described below, accommodate further advancement into the renal pelvis and major calyces to provide an effective stone fragment suction retrieval function.

Figure 5:
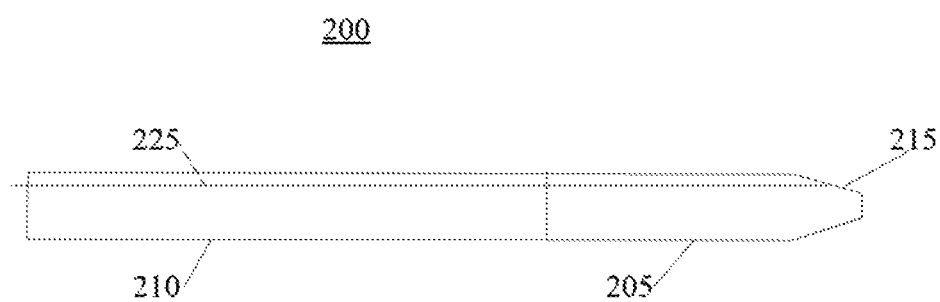
FIG. 5 is a cross section of an exemplary suction conduit of the present invention.
Figure 6A:
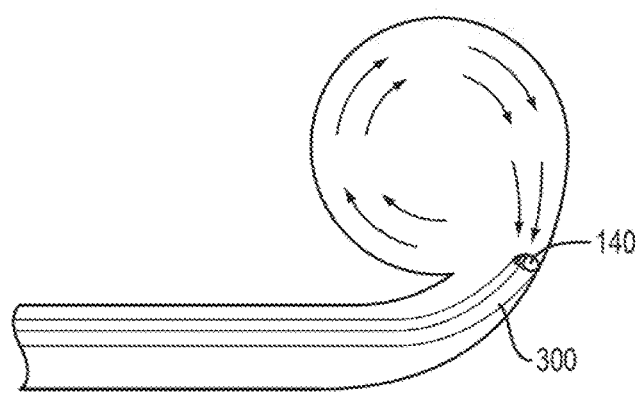
FIG. 6A is a side view of an embodiment of the present invention being manipulated within a patient's anatomy.
Figure 6B:
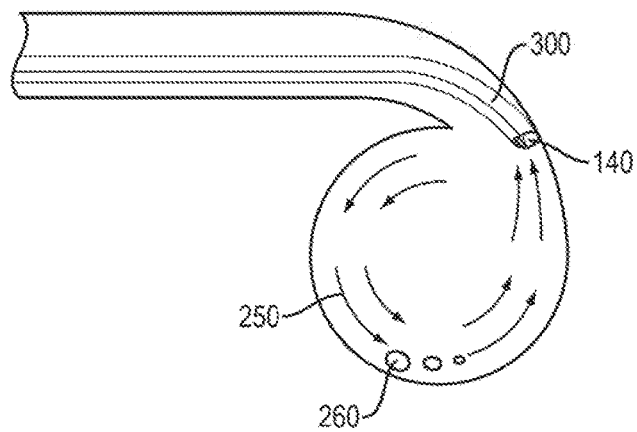
FIG. 6B is a side view of an embodiment of the present invention being manipulated within a patient's anatomy.
Figure 6C:
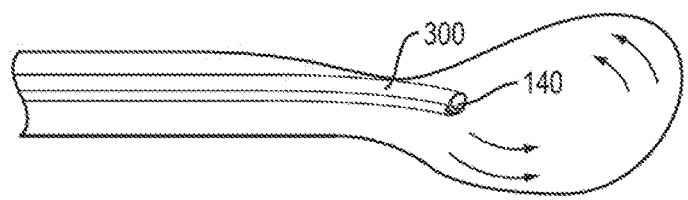
FIG. 6C is a side view of an embodiment of the present invention being manipulated within a patient's anatomy.

As shown in FIG. 5, an exemplary stone fragment suction device 200 is tubular in shape and includes a first portion 205 and a second portion 210. The first portion 205 includes a tip section 215. Positioned within a length of the stone fragment suction device 200 from the tip section 215 to a proximal end 220 is a pull cable 225. The second portion 210 is constructed to be non-collapsible and semi-rigid and the first portion 205 is constructed to be semi-flexible. The two portions 205, 210 enable the tip section 215 to be controlled by the pull cable 225 by a flexing of the first portion 205 while not affecting the second portion 210.

The tip section 215 can be configured to be substantially straight or have a preformed curve orientation. In some embodiments, the tip section 215 is selectively deflectable to enable placement of working channel openings directly opposite the lower poles of the kidney calyx. It is contemplated that the first portion 205 may be a slotted or folded wall tube section to enhance the flexibility of the distal end of the tube and enable different configurations to be achieved such as omnidirectional bending or directional bending.

Figure 8:
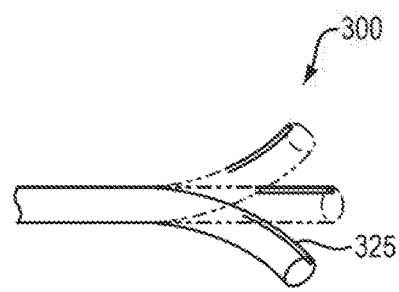
FIG. 8 is a side view of an embodiment of the present invention.

Although the stone fragment suction device 200 is shown with a single pull cable 225, other embodiments include multiple pull cables and a lockable control actuator to lock the tip section 215 at a desired deflection angle. One or more pull cables or wires may be positioned within stone fragment suction device 200 for manipulating in one or more directions. FIG. 8 illustrates an example of the device of the present invention provided with one pull cable 325. In this example, access sheath 300 is provided with a preformed tip angle.

Figure 7:
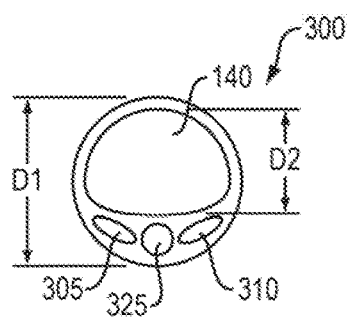
FIG. 7 is a cross sectional view of an embodiment of the present invention.

In some embodiments, it is contemplated that suction conduit 140 is non-circular in cross section, for example slightly oblong or ovular, as shown in FIG. 7. It is contemplated that the outer diameter D2 of the suction conduit 140 may be 11 or 12 Fr, ideally 12 Fr. It is contemplated that the outer diameter D1 of the access sheath may be 13 or 14 Fr. These sizes are chosen to be compatible with endoscopes or ureteroscopes. It is contemplated that the access sheath of the present invention may be used independent of an endoscope. It is contemplated that additional channels, for example, one or more irrigation channels, one or more visualization channels, or one or more pull cable channels may be oriented toward one end of the access sheath. It is contemplated that channels other than suction conduit 140 may terminate before the extreme distal tip of the access sheath. For example, additional channels may terminate 0.2-1.5 cm before the extreme distal tip of the access sheath. This may provide for the addition of a flap, surface deflection, an angle formed into the distal end of the irrigation channel, or otherwise add a directionality to the outflow of a fluid from the distal end of the irrigation supply channel.

FIGS. 6A-C and 7-8 illustrate access sheath 300 with a preformed tip angle being manipulated into different hard to reach calyces of the kidney. In one embodiment, far end 320 is abutted against a far wall of the calyx of the kidney. It is contemplated that irrigation fluid may be passed through irrigation channel 305 in a directed outflow resulting in organized fluid flow around the calyx in a direction 250, for example. This organized fluid flow direction 250 may help to clear small stones, stone fragments, or stone dust 260 by directing them toward the suction conduit 140 where active suction helps to pull the small stones, stone fragments, or stone dust 260 to substantially clear them from the kidney.

FIGS. 9A-9E, 10 11A-11B, 12, and 13 illustrate distal end regions of different embodiments of irrigation tip portions of the steerable access sheath of the present invention. Several targeted exit conduits 409, 429, 449, 469, 489, and 529 are provided about a distal end region of the irrigation portions and may be oriented at different angles in different embodiments in order to create targeted flow to remove stone fragments or debris that might be stuck in a certain region of a kidney following fragmentation or lithotripsy. It is contemplated that through the design modifications of the present invention, flow may be directed with the intent to move a stone burden (dust, debris) in a particular direction, such as toward the exit of the kidney or toward the suction orifice, for example at the distal end 25 of suction conduit 40.

Irrigation tip portions 400, 420, 440, 460, 480, 500, 520 and 540 are provided with distal end 402, 422, 442, 462, 482, 502, 522, or 542 which is soft, chamfered or curved as shown in 403, 423, 443, 463, 483, 503, 523, and 543 for patient comfort during insertion. Walls 405, 425, 445, 465, and 485 and contoured outermost edges 404, 424, 444, 464, 484, 504, 524, and 544 of targeted exit conduits 409, 429, 449, 469, 489, and 529 may be provided and arranged in order to facilitate the directionality of the directed fluid flow.

Figure 9D:
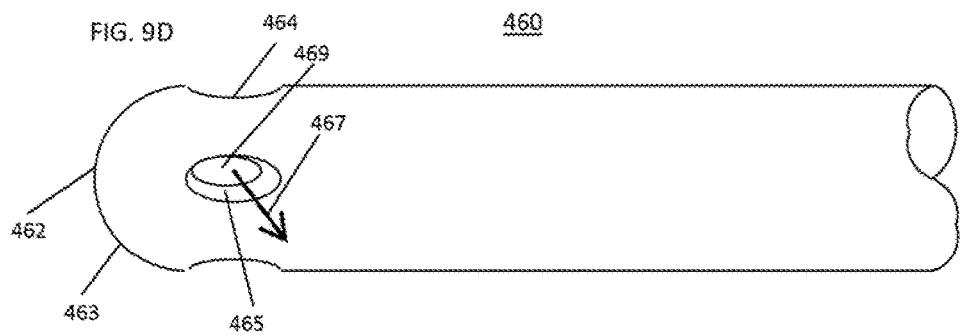
FIGS. 9D-9E are side views of embodiments of the present invention that target different exit angles for directed fluid flow.
Figure 9E:
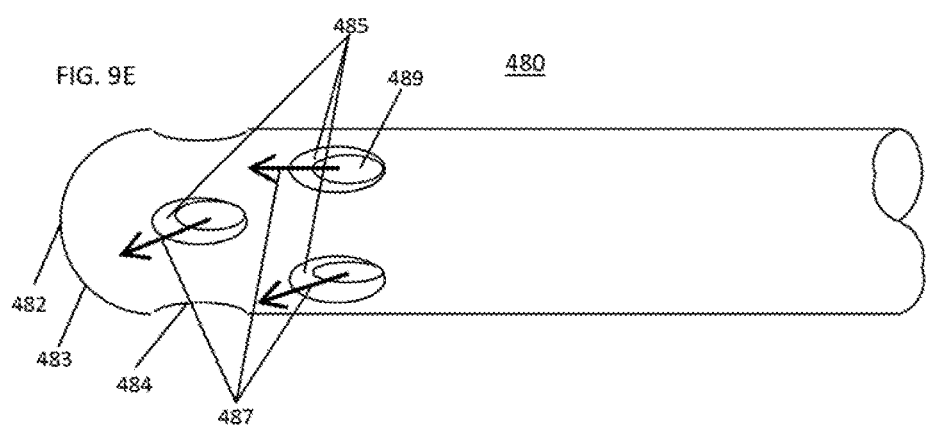

In FIG. 9A, the one or more targeted exit conduits being oriented substantially orthogonal to the longitudinal axis of the steerable access sheath. In FIGS. 9B and 9D, the targeted flow direction is generally toward the proximal end of the device. FIG. 9B shows direction of flow 427 toward the proximal end along the longitudinal axis and FIG. 9D shows direction of flow 467 angled proximally. In FIGS. 9C and 9E, the targeted flow direction is generally toward the distal end of the device. FIG. 9C shows direction of flow 447 toward the distal end along the longitudinal axis. FIG. 9E shows direction of fluid flow 487 angled distally. Targeted flow channels may be provided along a single cross sectional plane as illustrated in FIGS. 9A-9D or along several cross sectional planes as in 9E to achieve the desired fluid flow velocity and create a desired turbulence effect to more effectively clean out stone debris and stone dust from an anatomical region of interest, such as a kidney. It is contemplated that fluid flow velocities from 25 to 250 mL per second would be well suited to this purpose. The fluid inflow must match the fluid outflow or kidney damage due to positive/negative pressures may occur.

It is contemplated that the device of the present invention would be targeted at removing stone debris and stone dust that is less than about 2 mm in diameter. Most preferably the device of the present invention would be capable of removing stone debris and stone dust that is larger than 1 mm in diameter so as to eliminate the majority of debris and/or dust remaining following fragmentation or lithotripsy. It is contemplated that fluid flow into the patient would travel through fluid flow channel 170, for example, and that targeted exit conduits would be connected into the fluid flow channel such that fluid may exit equally from all targeted exit points. It is further contemplated that flow might be restricted in certain channels and unrestricted in other channels to further direct the flow. Subsequent suctioning to remove the outflow of fluid into the patient and any stone dust or stone debris may occur through central lumen 40, 140, or 155, for example.

Figure 10:
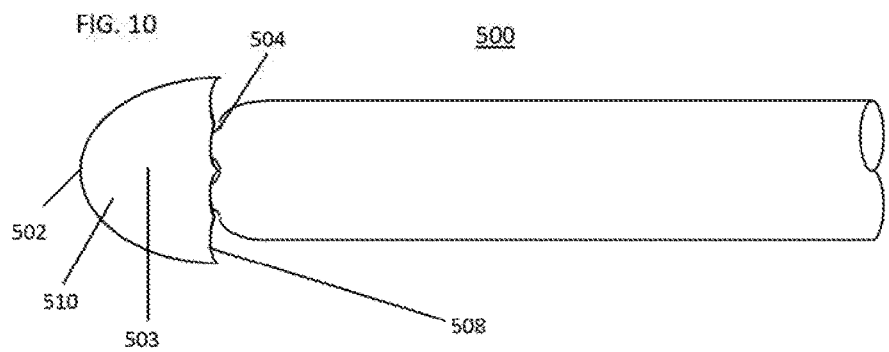
FIG. 10 is a side view of an embodiment of the present invention.
Figure 11A:
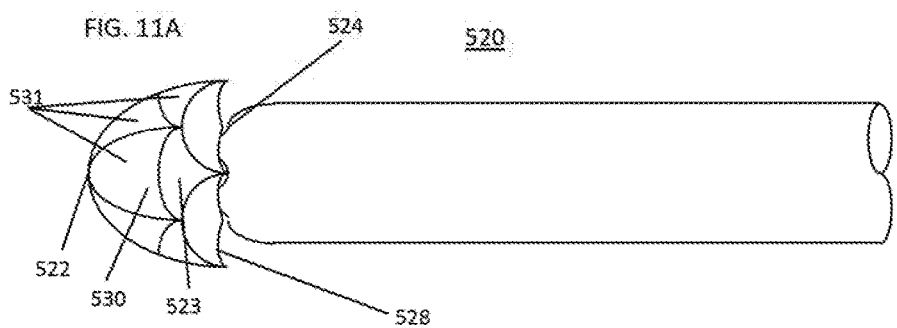
FIG. 11a is a side view of an embodiment of the present invention.

FIGS. 10-13 illustrate an alternative embodiment of the device of the present invention which is equipped with a mushroom shaped distal end. The mushroom shaped distal end 510, 530, and 550 are capable of forming into a closed position during insertion or removal (FIG. 11B) wherein the outside diameter of the device resulting from lateral protrusions 508, 528, 548 is reduced and forming into an open position wherein the lateral protrusions are extended during active fluid flow, suction, and/or stone removal (FIGS. 10, 11A, and 12). It is contemplated that several layers of polymer, silicone, or plasticized material formed into flaps 531, for example, may be used to accomplish this result. It is contemplated that the layers of material may be forced open by the active fluid flow and return to a resting closed state when active fluid flow is not occurring. Additional features may be included in the mushroom shaped head, including the targeted exit conduits shown in FIGS. 9A-9E, located at various positions through the mushroom shaped head to preferentially direct the fluid flow. The mushroom head may provide a more effective proximally directed fluid flow than the targeted exit conduits on their own. It is contemplated that application of some fluid pressure during insertion may keep the one or more inflow lumens inflated and stiff in their preferred orientation. Conversely, if little or no fluid inflow is provided during insertion, when inflow begins it may be likely that the inflow lumens would inflate and deploy and even if folded back a bit from insertion, the inflow lumens would be able to fully inflate and deploy.

FIG. 12 illustrates a cross sectional view of irrigation tip portion 520, in which central lumen wall 521 supports mushroom shaped head 530 within the outer wall of irrigation tip portion 520. Mushroom shaped head 530 is supported within the access sheath main lumen with extensions 525. Gap 526 is provided at the base of mushroom shaped head 530 to allow for the flow of fluid out from the device into a patient's anatomy. It is contemplated that additional exit conduits may be placed at the distal most end 522 of the steerable access sheath to direct fluid in line with the longitudinal axis of the access sheath.

FIG. 13 illustrates direction of fluid flow 527 which is targeted axially around mushroom shaped head 530 through targeted exit conduits 529 in irrigation tip portion 520. Fluid enters through central lumen 532 into mushroom head and is distributed through targeted exit conduits 529. Central lumen wall 532 may help to guide the fluid flow into the targeted exit conduits 529.

Figure 14:
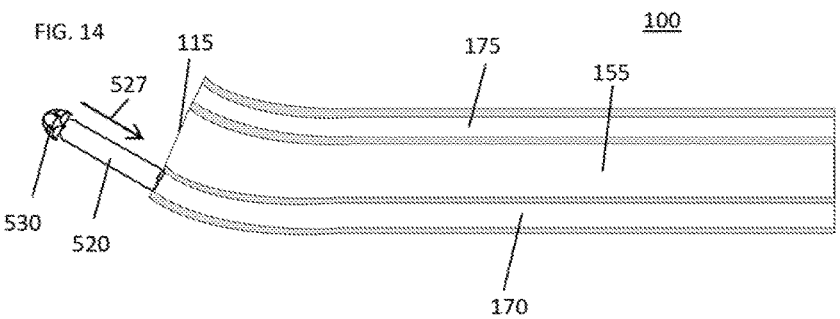
FIG. 14 is a cross sectional view of an embodiment of the present invention.

FIGS. 14-17 illustrate how irrigation tip portion 400, 420, 440, 460, 480, 500, 520, and 540 may be integrated into access sheath 10, 100, 200, or 300. FIG. 14 illustrates irrigation tip portion 520 with mushroom shaped head 530 extending distally from fluid inflow channel 170 to create a fluid flow path 527 which may help return stone fragments and stone debris to suction conduit 155.

Figure 15:
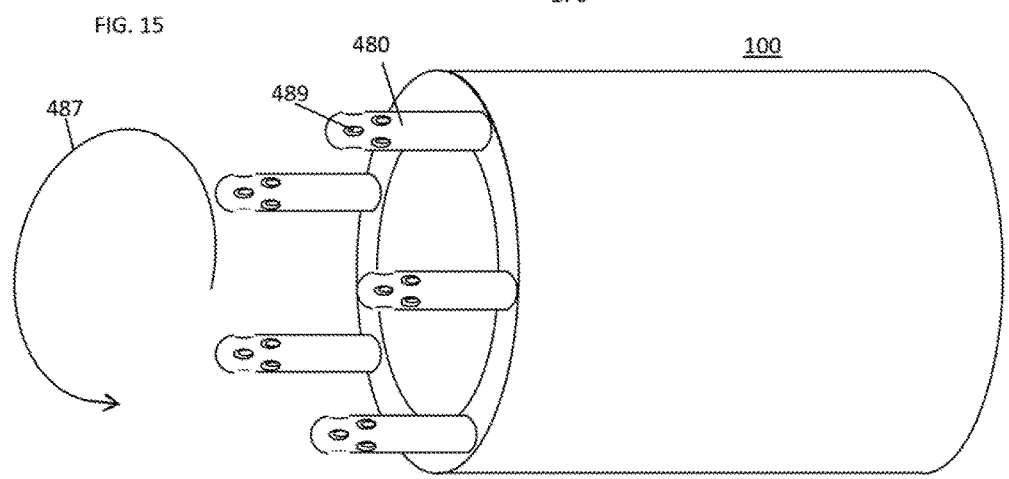
FIG. 15 is a perspective view of an embodiment of the present invention.

FIG. 15 illustrates a plurality of irrigation tip portions 480 protruding from a distal region of steerable access sheath 100. Targeted exit conduits 489 located toward a distal end of irrigation tip portions 480 help guide fluid flow in direction 487 to create turbulence or a vortex at the distal end of steerable access sheath 100. In this embodiment, fluid flow is in a direction around and in front of the tip of the access sheath and active suction may help to draw stone debris or stone dust back into suction conduit 155 to remove it from a patient. It is contemplated that irrigation tip portions 480 may be movable further into and subsequently withdrawn from the distal end of steerable access sheath 100. Movement of irrigation tip portions 480 may further aid in stirring up debris to be removed from difficult to reach locations. Such irrigation tips may have slight pre-existing bends for better steering of tip into difficult to reach locations.

Figure 16:
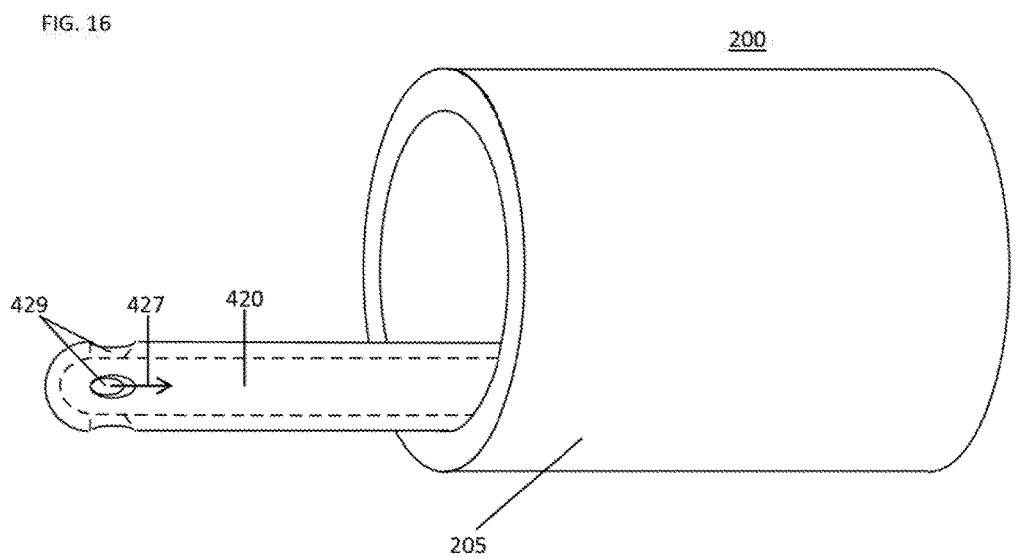
FIG. 16 is a perspective view of an embodiment of the present invention.

FIGS. 16 and 17 illustrate embodiments wherein irrigation portions 420 and 520, respectively, are inserted within a central suction conduit as an accessory instrument. In this embodiment, stone fragment suction device 200 is provided with control means at a proximal end for advancing and retracting irrigation portions 420 and 520 as appropriate to encourage the creation of turbulence to remove stone fragments and stone debris. Typically irrigation portions 420 and 520 would be maintained within the central suction lumen during insertion and removal of stone fragment suction device 200 into and out of a patient's tortuous anatomy. Mushroom shaped head 530 and targeted exit conduits 429 help to encourage fluid flow back into central suction lumen to facilitate removal of unwanted debris from a patient.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

What is claimed is:

1. An apparatus comprising:
   a steerable access sheath, the steerable access sheath comprising:
      a proximal end, a distal end, a tip at the distal end, a central lumen, and an outer lumen;
      a suction conduit positioned within the central lumen, the suction conduit extending from the distal end to the proximal end;
      the outer lumen having one or more channels therethrough, the central lumen positioned in the outer lumen;
      at least a portion of the one or more channels being fluid flow channels; and
      the one or more fluid flow channels extending from the proximal end to the distal end, the one or more fluid flow channels including one or more targeted exit conduits and in fluid communication with the one or more fluid flow channels proximal to the tip, and the one or more targeted exit conduits having exit pathways oriented to create a directed flow at the distal tip, wherein the one or more fluid flow channels are configured to generate turbulence within a region of interest.

2. The apparatus of claim 1, wherein at least one of the one or more targeted exit conduits are angled toward the distal end of the steerable access sheath.

3. The apparatus of claim 2, wherein the one or more targeted exit conduits are arranged in multiple planes parallel to the cross section of the steerable access sheath.

4. The apparatus of claim 3, wherein the tip further comprises a soft edge for ease of insertion.

5. The apparatus of claim 4, wherein the tip is selectively deflectable to enable specific placement of the suction conduit.

6. The apparatus of claim 5, wherein the suction conduit comprises a steering mechanism selected from the group consisting of one or more cables and a lockable control actuator.

7. The apparatus of claim 1, wherein at least one of the one or more targeted exit conduits are angled toward the proximal end of the steerable access sheath.

8. The apparatus of claim 7, wherein the tip further comprises a mushroom shaped flap.

9. The apparatus of claim 8, wherein the mushroom shaped flap collapses to a collapsed state during insertion and expands to expanded state during active fluid flow.

10. The apparatus of claim 9, wherein the mushroom shaped flap further comprises an exit port for fluid flow at a distal most end of the steerable access sheath.

11. The apparatus of claim 1, wherein the one or more targeted exit conduits are arranged in a single plane parallel to a cross section of the steerable access sheath.

12. The apparatus of claim 1, wherein the angle of the targeted exit conduits with respect to the longitudinal axis of the steerable access sheath varies across each of the one or more targeted exit conduits.

13. The apparatus of claim 1, wherein the suction conduit is tapered with decreasing diameters from the proximal end to the distal end of the steerable access sheath.

14. The apparatus of claim 1, further comprising:
   a channel positioned within the outer lumen of the steerable access sheath from the distal end to the proximal end;
   one or more fiberoptic imaging fibers positioned within a length of the lumen; and
   one or more light carrying fibers positioned within a length of the lumen.

15. An apparatus comprising:
   an access sheath, the access sheath comprising: a proximal end, a distal end, a tip at the distal end, a central lumen, and an outer lumen;
   a suction conduit positioned within the central lumen from the distal end to the proximal end;
   a radiopaque material at the distal end to enable tracking with a remote fluoroscopic device;
   the outer lumen having one or more channels therethrough;
   at least a portion of the one or more channels being fluid flow channels, the one or more fluid flow channels extending from the proximal end to the distal end, the one or more fluid flow channels including a plurality of targeted exit conduits at a distal end.

16. The apparatus of claim 15, wherein an outer circumference of the central lumen and an outer circumference of the outer lumen form concentric circles.

17. The apparatus of claim 15, wherein the access sheath has one or more irrigation tips provided with targeted exit conduits that are extendable from a distal portion of the access sheath.

18. The apparatus of claim 15, wherein the suction conduit comprises at least half the volume of the access sheath.

19. A method for removing stone dust and stone debris from a patient, the method comprising:
   inserting the steerable access sheath of claim 15 into a patient;
   steering the distal tip of the access sheath to an area of interest;
   directing fluid through the one or more fluid flow channels and creating turbulence at the tip through the targeted exit conduits; and
   using active suction to remove the stone dust and stone debris.

* * * * *